United States Patent [19]
Phillips

[11] Patent Number: 5,438,980
[45] Date of Patent: Aug. 8, 1995

[54] INHALATION/EXHALATION RESPIRATORY PHASE DETECTION CIRCUIT

[75] Inventor: Steven L. Phillips, Olathe, Kans.

[73] Assignee: Puritan-Bennett Corporation, Lenexa, Kans.

[21] Appl. No.: 3,129

[22] Filed: Jan. 12, 1993

[51] Int. Cl.⁶ .............................................. A61M 16/00
[52] U.S. Cl. ........................... 128/204.23; 128/204.21
[58] Field of Search ....................... 128/204.18, 204.21, 128/204.23, 207.18

[56] References Cited

U.S. PATENT DOCUMENTS

| | | | |
|---|---|---|---|
| 3,500,073 | 3/1970 | Salaman | 307/268 |
| 3,896,800 | 7/1975 | Cibulka | 128/145 |
| 3,952,739 | 4/1976 | Cibulka | 128/204.23 |
| 3,976,064 | 8/1976 | Wood et al. | 128/204.21 |
| 4,050,458 | 9/1977 | Friend | 128/204.23 |
| 4,082,093 | 4/1978 | Fry et al. | 128/204.26 |
| 4,207,884 | 6/1980 | Isaacson | 128/204.26 |
| 4,281,651 | 8/1981 | Cox | 128/204.23 |
| 4,393,869 | 7/1983 | Boyarsky et al. | 128/204.21 |
| 4,448,192 | 5/1984 | Stawitcke et al. | 128/204.26 |
| 4,459,982 | 7/1984 | Fry | 128/204.23 |
| 4,527,557 | 7/1985 | DeVries et al. | 128/204.23 |
| 4,611,591 | 9/1986 | Inui et al. | 128/205.24 |
| 4,617,924 | 10/1986 | Heim et al. | 128/204.23 |
| 4,635,631 | 1/1987 | Izumi | 128/204.23 |
| 4,648,395 | 3/1987 | Sato et al. | 128/204 |
| 4,681,099 | 7/1987 | Sato et al. | 128/204.23 |
| 4,686,975 | 8/1987 | Naimon et al. | 128/204.23 |
| 4,784,130 | 11/1988 | Kenyon et al. | 128/204.21 |
| 4,886,056 | 12/1989 | Simpson | 128/201.25 |
| 4,986,269 | 1/1991 | Hakkinen | 128/204.23 |
| 5,016,626 | 5/1991 | Jones | 128/204.26 |
| 5,048,515 | 9/1991 | Sanso | 128/204.18 |
| 5,065,746 | 11/1991 | Steen | 128/205.24 |
| 5,065,756 | 11/1991 | Rapoport | 128/204.18 |
| 5,099,837 | 3/1992 | Russel, Sr. et al. | 128/204.18 |
| 5,107,830 | 4/1992 | Younes | 128/204.18 |
| 5,107,831 | 4/1992 | Halpern et al. | 128/204.26 |
| 5,117,819 | 6/1992 | Servidio et al. | 128/204.18 |
| 5,129,390 | 7/1992 | Chopin et al. | 128/204.21 |
| 5,134,995 | 8/1992 | Gruenke et al. | 128/204.23 |
| 5,148,802 | 9/1992 | Sanders et al. | 128/204.18 |
| 5,161,525 | 11/1992 | Kimm et al. | 128/204.23 |
| 5,199,424 | 4/1993 | Sullivan et al. | 128/204.23 |
| 5,239,995 | 8/1993 | Estes et al. | 128/204.23 |

FOREIGN PATENT DOCUMENTS

| | | |
|---|---|---|
| 0324275 | 7/1989 | European Pat. Off. . |
| 0360885 | 4/1990 | European Pat. Off. . |
| 0521314A1 | 1/1993 | European Pat. Off. . |
| 2238472 | 2/1975 | France . |

Primary Examiner—Edgar S. Burr
Assistant Examiner—Aaron J. Lewis
Attorney, Agent, or Firm—Fulwider Patton Lee & Utecht

[57] ABSTRACT

An apparatus (10) for controlling the pressure of a respiratory gas delivered to a patient includes a phase detection circuit (24) for determining the inhalation and exhalation phases of the patient's respiratory cycle. More particularly, a flow signal representative of the respiratory flow is compared to second signal, offset in time and scaled in magnitude relative to the flow signal, in order to determine the transition from one phase to the next.

27 Claims, 5 Drawing Sheets

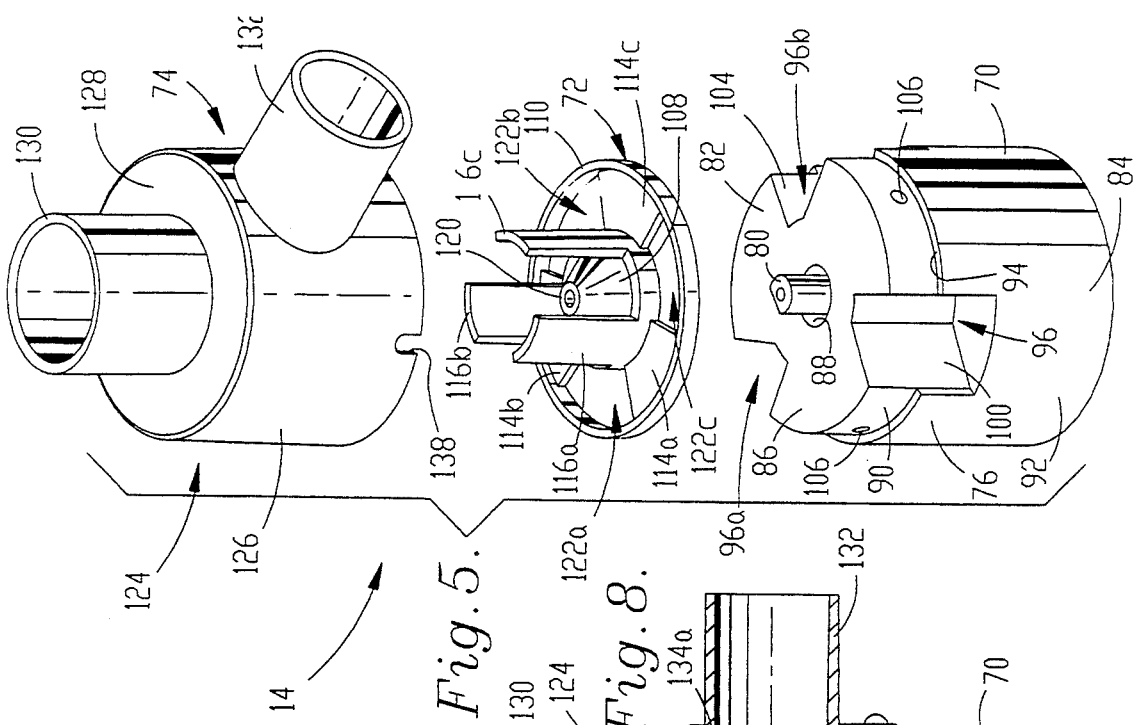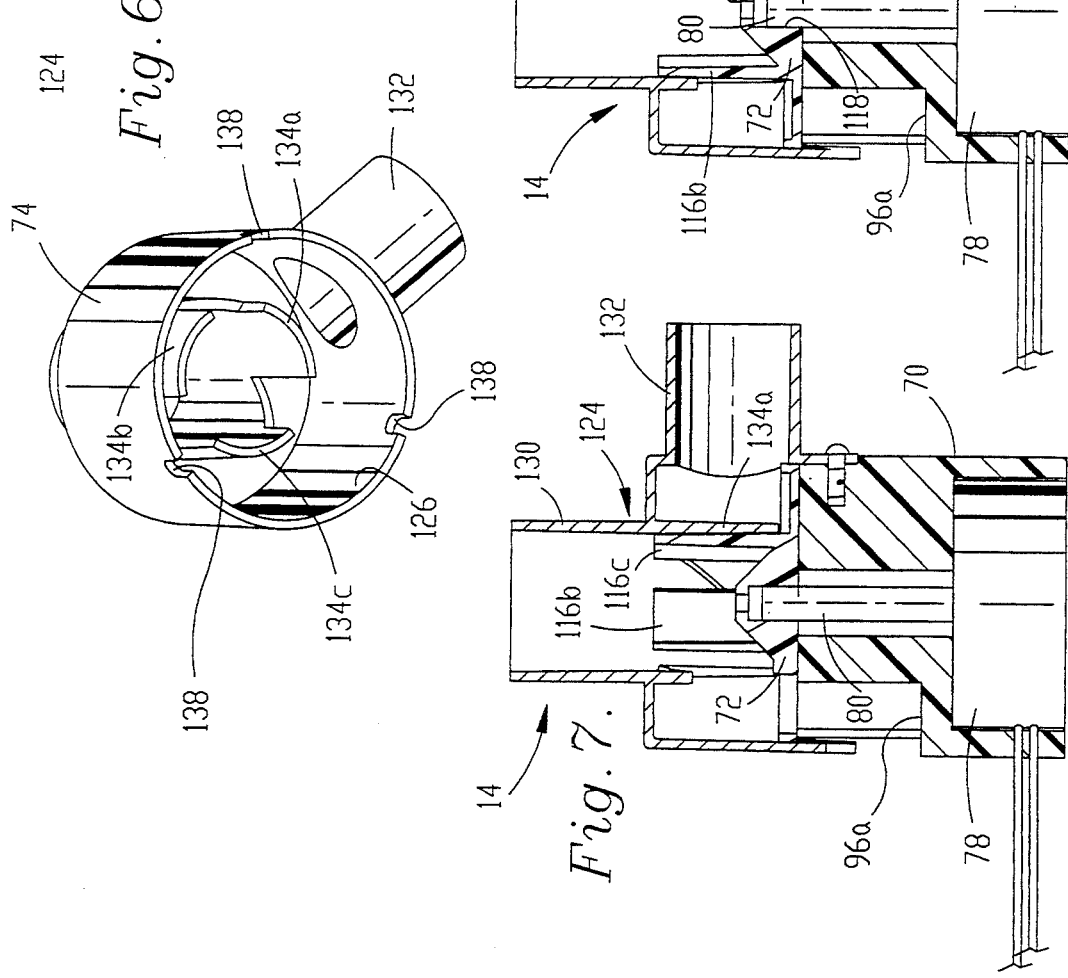

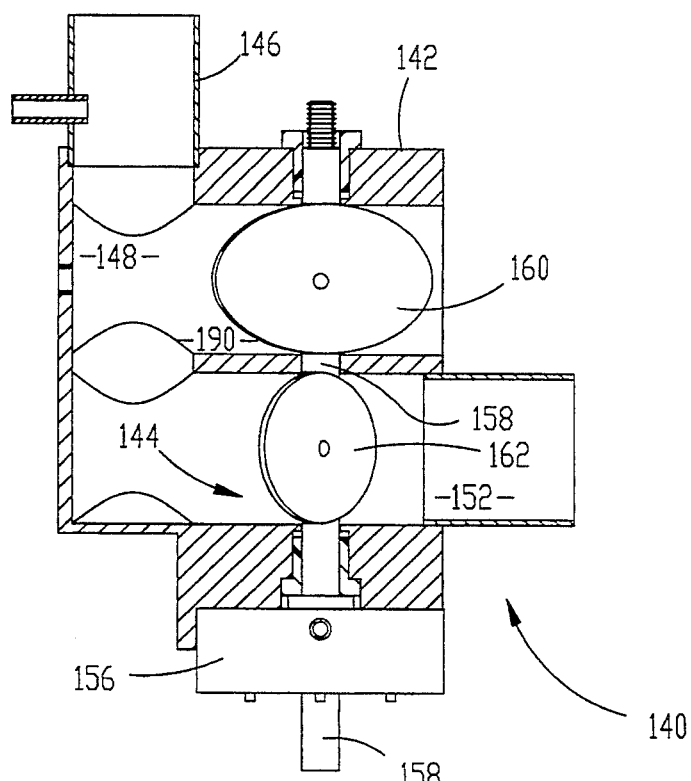
Fig.11.
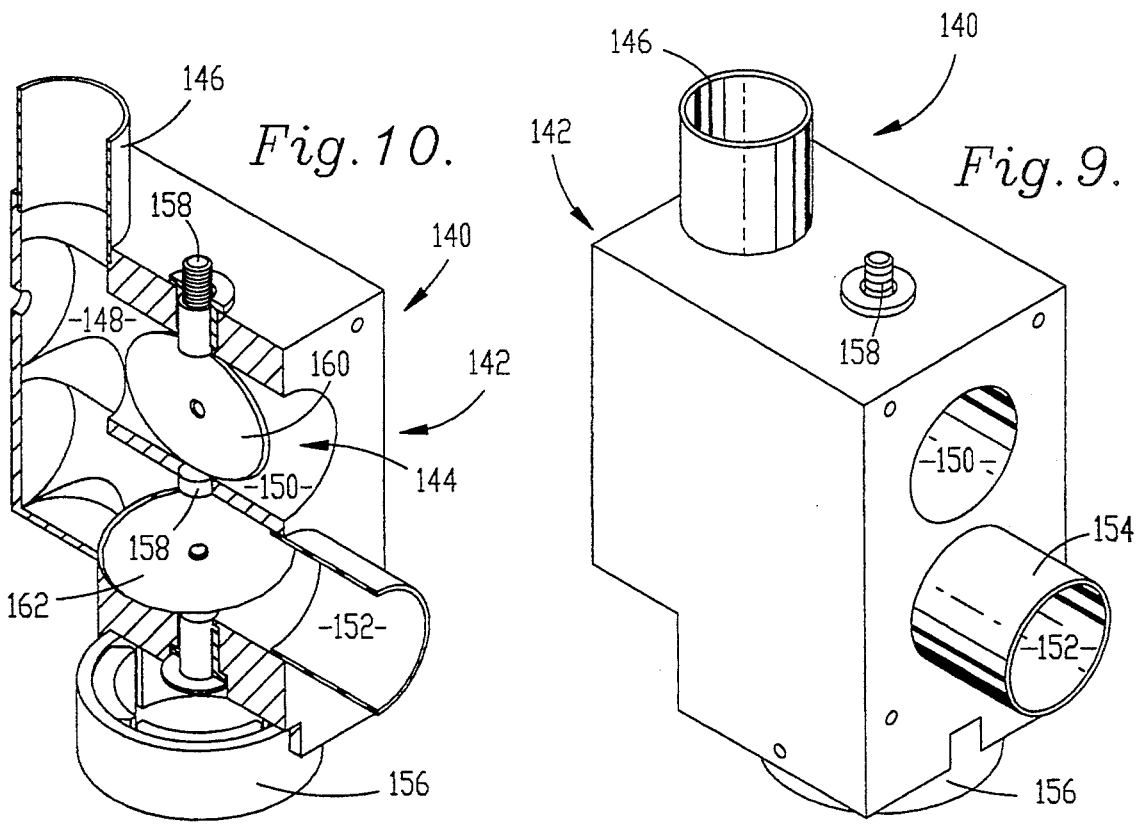
Fig.10.
Fig.9.

INHALATION/EXHALATION RESPIRATORY PHASE DETECTION CIRCUIT

BACKGROUND OF THE INVENTION

1. Field of the Invention

The present invention is concerned with an apparatus for controlling the pressure of a respiratory gas delivered to a patient. More particularly, the preferred apparatus includes a trigger circuit for determining the inhalation and exhalation phases of the patient's respiratory cycle.

2. Description of the Prior Art

Obstructive sleep apnea is a sleep disorder characterized by relaxation of the airway including the genioglossus throat muscle during sleep. When this occurs, the relaxed muscle can partially or completely block the patient's airway. Partial blockage can result in snoring or hypopnea. Complete blockage results in obstructive sleep apnea.

When complete blockage occurs, the patient's inhalation efforts do not result in the intake of air and the patient becomes oxygen deprived. In reaction the patient begins to awaken. Upon reaching a nearly awakened state, the genioglossus muscle resumes normal tension which clears the airway and allows inhalation to occur. The patient then falls back into a deeper sleep whereupon the genioglossus muscle again relaxes and the apneic cycle repeats. In consequence, the patient does not achieve a fully relaxed deep sleep session because of the repetitive arousal to a nearly awakened state. People with obstructive sleep apnea are continually tired even after an apparently normal night's sleep.

In order to treat obstructive sleep apnea, a system of continuous positive airway pressure (CPAP) has been devised in which a prescribed level of positive airway pressure is continuously imposed on the patient's airway. The presence of such positive pressure provides a pressure splint to the airway in order to offset the negative inspiratory pressure that can draw the relaxed airway tissues into an occlusive state. The most desired device for achieving a positive airway connection is the use of a nasal pillow such as that disclosed in U.S. Pat. No. 4,782,832, hereby incorporated by reference. The nasal pillow seals with the patient's nares and imposes the positive airway pressure by way of the nasal passages. The nasal pillow also includes a small vent for continuously exhausting a small amount of air in order to prevent carbon dioxide and moisture accumulation.

In the CPAP system, the patient must exhale against the prescribed positive pressure. This can result in patient discomfort, especially at the higher pressure levels. Because of this problem, the so-called bi-level positive airway pressure (BiPAP) system has been developed in which the pressure is lowered during the exhalation phase of the respiratory cycle. Practical implementation of the BiPAP system has met with only marginal success because of the difficulty in accurately and reliably detecting the occurrence of the exhalation and inhalation phases of the respiratory cycle. Respiratory phase detection has been a problem because the continual air exhaust at the nasal pillow, and other system leaks, results in a net positive air flow to the patient. Thus, phase transition cannot be determined merely on the basis of a change in the direction of air flow.

SUMMARY OF THE INVENTION

The apparatus of the present invention solves the prior art problems discussed above and provides a distinct advance in the state of the art. More particularly, the apparatus hereof reliably determines inhalation and exhalation phases in the respiratory cycle in order to control respiratory gas pressure in response.

The preferred embodiment of the invention hereof includes a gas supply for supplying a respiratory gas under pressure from a source thereof to a patient, a phase detection circuit for detecting the inhalation and exhalation respiratory phases, and a pressure controller for controlling the pressure delivered to the patient in a predetermined manner correlated with the respiratory phases.

The preferred phase detection circuit produces first and second signals representative of respiratory gas flow with these signals being time displaced relative to one another and scaled in magnitude. With this configuration, the signals present different gains and voltage offsets relative to one another during respective phases of the respiratory cycle. These two signals are compared to determine transitions, which correlate with transitions from one respiratory phase to another. With reliable phase detection, the gas pressure delivered to the patient is controlled in accordance with the phases.

BRIEF DESCRIPTION OF THE DRAWINGS

FIG. 5 is an exploded perspective view of the major components of the preferred valve of FIG. 1;

FIG. 6 is a lower perspective view of the inlet/outlet housing of the valve of FIG. 5;

FIG. 7 is a partial sectional view of the assembled valve of FIG. 5 illustrating the shiftable components in a first position;

FIG. 8 is a partial sectional view of the assembled valve of FIG. 5 illustrating the shiftable components in a second position;

FIG. 9 is a perspective view of a second embodiment of the valve of FIG. 1;

FIG. 10 is a cut-away perspective view of the valve of FIG. 9; and

FIG. 11 is a sectional view of the valve of FIG. 9.

DETAILED DESCRIPTION OF THE PREFERRED EMBODIMENT

Figure 1:
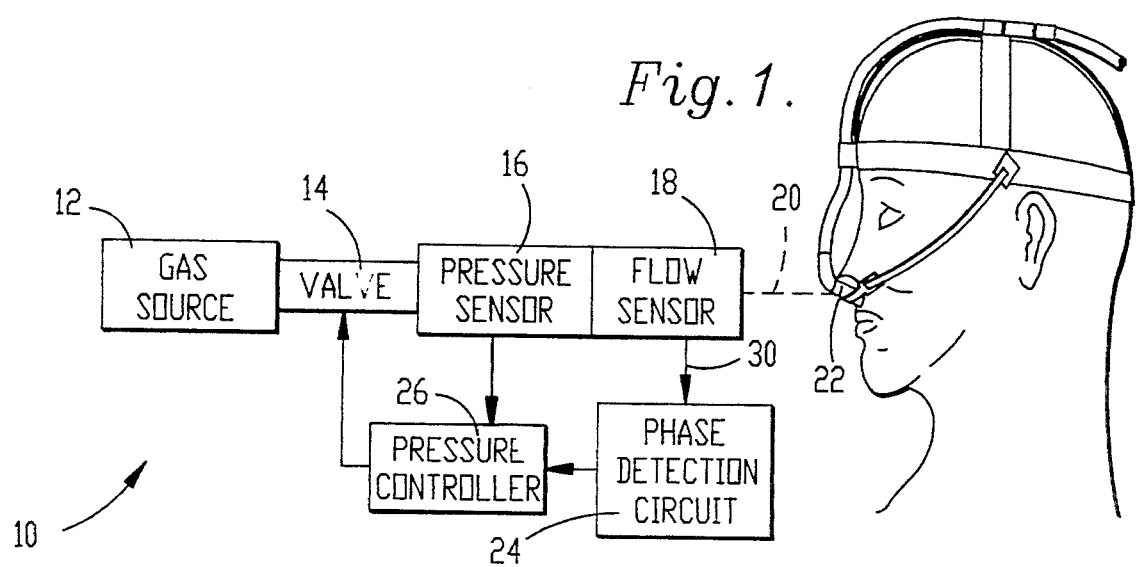
FIG. 1 is a schematic representation of the preferred apparatus for facilitating the respiration of a patient.

Referring initially to FIG. 1, apparatus 10 includes gas source 12, control valve 14, pressure sensor 16 and flow sensor 18 coupled with a so-called ADAM circuit available from Puritan Bennett Corp. of Lenexa, Kans., which includes pneumatic hose 20 and nasal pillow 22. Apparatus 10 further includes phase detection circuit 24 and pressure controller 26. In the preferred embodiment, components 12–18 and 24–28 are enclosed in a single housing to which the ADAM circuit is coupled.

Gas source is preferably a variable speed blower operable to produce 120 liters per minute at 30 cm. water pressure. The preferred pressure sensor 16 is available from Sensym Company as model number SCX01. Flow sensor 18 is preferably model AWM2300 available from Microswitch Corp., transducer operable for producing an electrical signal on line 30 representative of the air flow therethrough and thereby representative of the air flow delivered to the patient.

Figure 2:
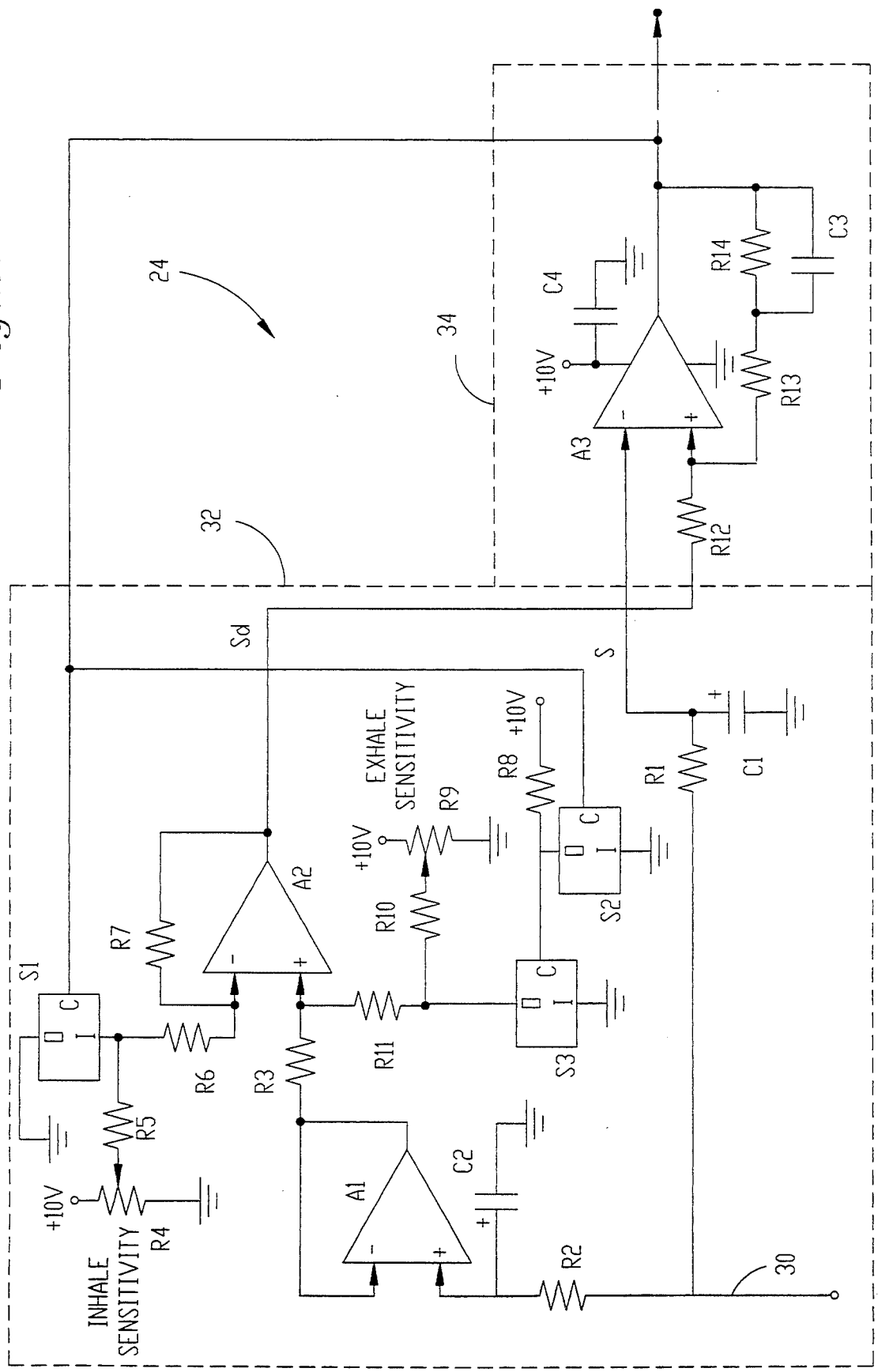
FIG. 2 is an electrical schematic of the preferred phase detection circuit of the apparatus of FIG. 1.

FIG. 2 is an electrical schematic of phase detection circuit 24 which includes signal production circuit 32 and signal processing circuit 34. Signal production circuit 32 receives the flow signal from flow sensor 18 by way of line 30. This signal is filtered for noise and other transients by resistor R1 (22K) and capacitor C1 (1 uF) connected as shown in FIG. 2 and delivered as signal "S" to signal processing circuit 34.

Signal production circuit 32 also transforms the flow sensor signal into an offset signal "Sd" which is delayed in time and scaled in magnitude relative to signal S. Initially the flow sensor signal is time delayed by 200 milliseconds using resistor R2 (100K) and capacitor C2 (2.2 uF) interconnected as shown. The relative time delay between time signals S and Sd is illustrated by the graphs in FIG. 3.

The time delayed signal is then delivered to the positive input terminal of amplifier A1 (type 358A) with the output therefrom connected as feedback to a negative input terminal. The output of amplifier A1 is also connected to output resistor R3 (221K). Amplifier A1 functions as a voltage follower to provide a high impedance input to the flow signal.

Figure 3:
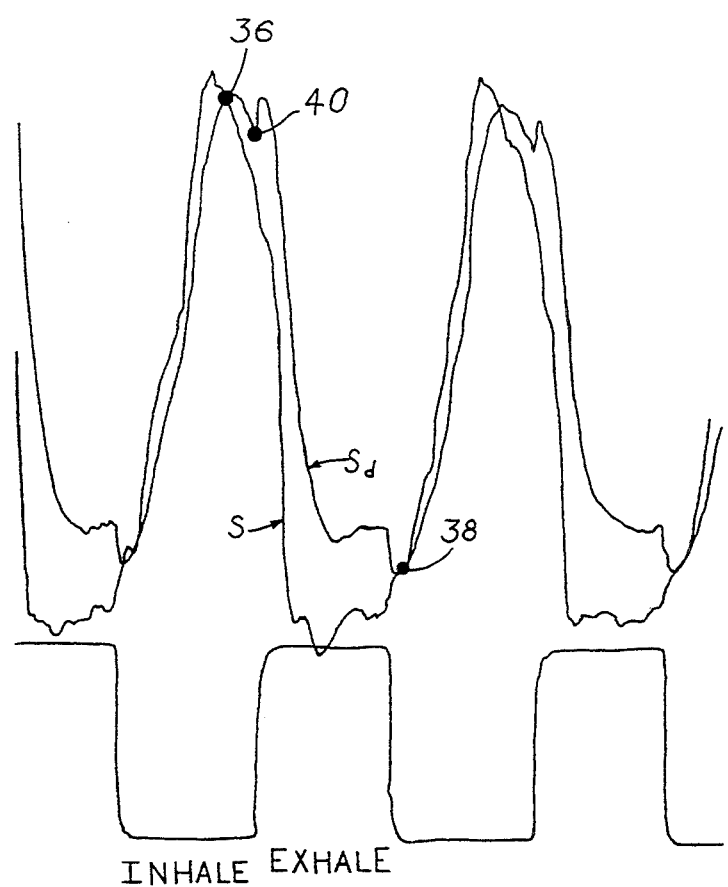
FIG. 3 is a graph illustrating the flow and offset signals of the detection circuit of FIG. 2 and illustrating patient inhalation and exhalation phases.

The conditioned time delay signal is then processed to scale the magnitude thereof so that signal Sd presents lower amplitude than signal S during the inhalation phase, and so that signal Sd presents a higher amplitude than signal S during the exhalation phase as illustrated in FIG. 3. To accomplish this, the gain of the signal is changed independently for the inhalation and exhalation portions of the signal and a variable offset is added by the sensitivity potentiometers R4 and R9.

As discussed further hereinbelow, the output from phase detection circuit 24 produces a logic high output during exhalation and a logic low during inhalation. These outputs are also provided as feedback to signal production circuit 32, specifically to control terminal C of CMOS inhalation switch S1 and to control terminal C of CMOS switch S2. These CMOS switches are type 4066B and operate so that when a logic high input is provided to terminal C, the switch is "on," that is, connection is made between terminals "I and O" thereof. When terminal C is low, the connection between terminals I and O is open.

During inhalation, terminal C of switch S1 is low and the switch is off. Voltage is then supplied to the negative input terminal of amplifier A2 (type 358A) by way of inhale sensitivity potentiometer R4 (500 Ohms full scale), resistor R5 (10K) and resistor R6 (221K). Resistor R7 (221K) interconnects the output of amplifier A2 with the negative input terminal thereof. The level of the voltage delivered to negative input terminal of amplifier A2 determines the amplitude scaling of the delayed flow sensor signal delivered to the positive input terminal. More specifically, potentiometer R4 is adjusted to provide the desired offset of output signal Sd relative to signal S during inhalation.

Also during inhalation, the logic low signal is delivered to terminal C of switch S2, which turns this switch off. In turn, a logic high signal is imposed on terminal C of CMOS switch S3 by way of resistor R8 (10K). This turns on switch S3 which imposes ground potential on the voltage output from potentiometer R9 and resistor R10 and thereby disables the exhale sensitivity portion of the circuit.

During exhalation, a logic high signal is delivered to terminal C of switch S1 which then turns on and imposes ground potential on the voltage output from potentiometer R4 and resistor R5 in order to disable the inhalation sensitivity portion of the circuit. The logic high exhalation signal also turns on switch S2 which imposes ground potential on the voltage output from resistor R8. In turn, switch S3 turns off. This allows exhale sensitivity voltage to be delivered to the positive input terminal of amplifier A2 by way of exhale sensitivity potentiometer R9 (500 Ohms full scale), resistor R10 (10K) and resistor R11 (221K). Potentiometer R9 is adjusted to provide the desired offset of signal Sd relative to signal S during inhalation.

As illustrated in the graph of FIG. 3, signal production circuit 32 produces signals S and Sd so that the voltage level of signal Sd is less than that of signal S during inhalation. Conversely, the voltage level of signal S is less than that of signal Sd during exhalation.

Signal processing circuit 34 receives signals S and Sd and compares these signals to determine the occurrence of the inhalation and exhalation phases of the respiratory cycle. Specifically, signal S is received at the negative input terminal of comparator A3 (type 358A) and signal Sd is received at the positive input terminal thereof by way of resistor R12 (100K). When the voltage level of signal S is greater than that of signal Sd, the output from comparator A3 is logic low and inhalation is indicated thereby. When the voltage level of signal Sd is the greater of the two, comparator A3 output goes high and exhalation is indicated.

Resistor R13 (100K), resistor R14 (10 m), and capacitor C3 (2.2 uF) are interconnected with comparator A3 as illustrated in FIG. 2 and provide a signal blanking interval after a transition in the output of comparator A3. More particularly, resistor R13 and capacitor C3 provide increased voltage hysteresis in the delivery of feedback from the output to the positive input terminal of comparator A3 in order to eliminate false triggering due to transients, noise or the like. Capacitor C4 (100 nF) provides input smoothing for the supply voltage delivered to comparator A3.

An inspection of the graphs of signals S and Sd in FIG. 3 illustrates crossover points 36 and 38, and artifact 40 at the inhalation peak in signal Sd. Crossover points 36,38 are determined by the time delay imposed by resistor R2 and capacitor C2, by the amplitude scaling, and by the offset voltages which can be adjusted by potentiometers R4 and R9 for the respective phases. Artifact 40 corresponds to the phase change from inhalation and exhalation, and occurs because of the transition of signal production circuit 32 between the inhalation and exhalation offset modes. The time delay from crossover 36 to artifact 40 corresponds to the blanking interval determined by the hysteresis of comparator A3 as set by resistors R12, R13 and R14. Phase detection circuit 24 provides an output on line 42 representative of the inhalation and exhalation phases of the patient. More particularly, circuit 24 provides a logic high output at +10 VDC during exhalation and a logic low output at 0 volts during inhalation.

Figure 4:
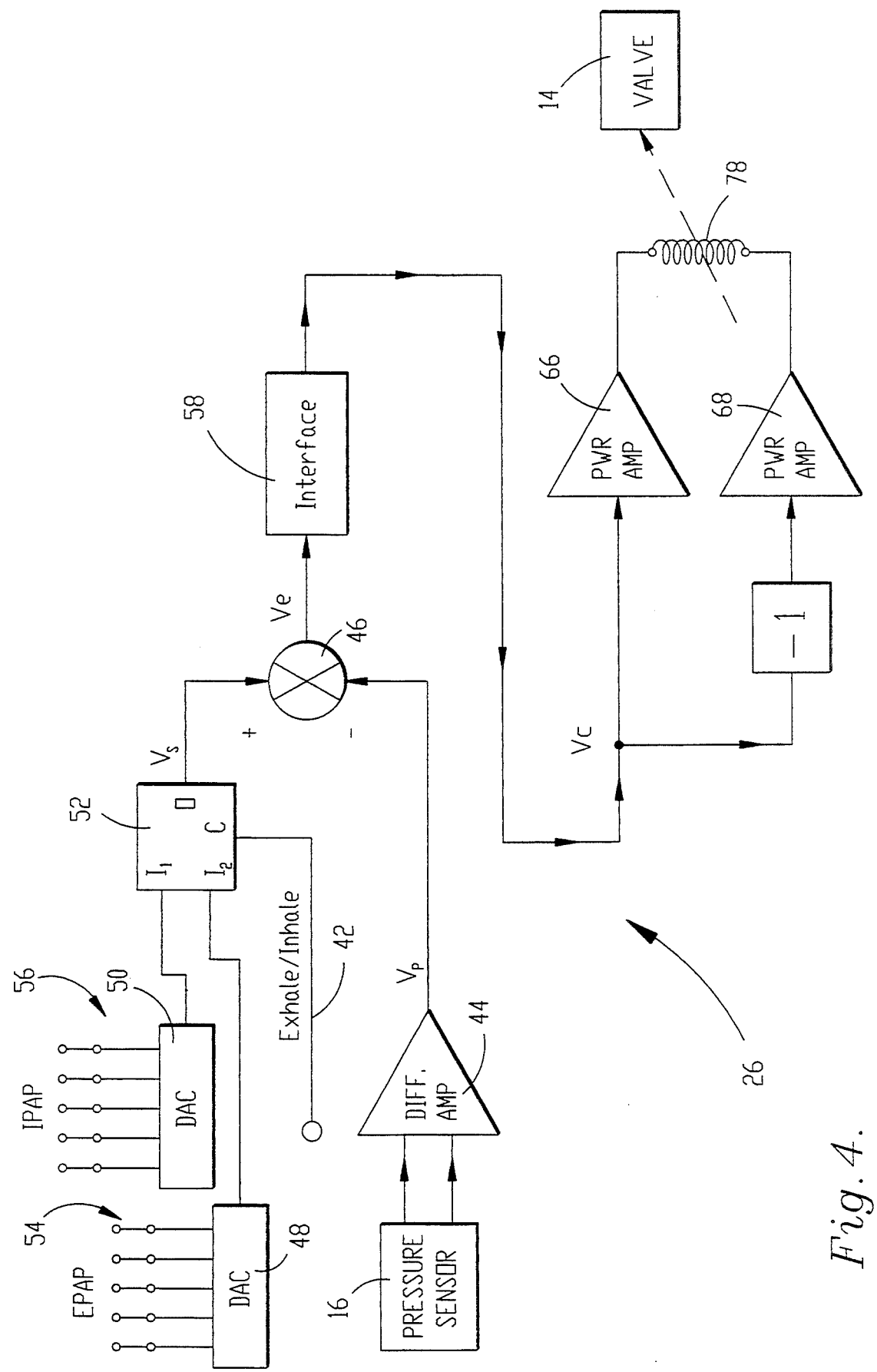
FIG. 4 is an electrical block diagram illustrating the preferred pressure controller of FIG. 1.

FIG. 4 is an electrical block diagram illustrating pressure controller 26, control valve 14 and pressure sensor 16. In general, controller 26 receives signals from phase detection circuit 24 and pressure sensor 16 and, in response, operates valve 14 to maintain the respective inhalation and exhalation pressures delivered to the patient.

Pressure sensor 16 provides a pair of differential voltage signals to the corresponding inputs of differential amplifier 44 that responds by providing a voltage output (Vp) to error detector 46 representative of the pressure being delivered to the patient. Conventional error detector 46 compares the pressure signal Vp with a set point pressure signal Vs in order to produce error signal Ve.

Set point signal Vs is produced by digital-to-analog converter (DAC) 48, DAC 50 and CMOS switch 52. DAC 48 receives a digital input representative of the desired exhalation positive air pressure (EPAP) by way of a set of five DIP switches 54, and converts the digital output to a representative analog signal delivered to terminal I2 of switch 52. Similarly, DAC 50 receives its digital input for inhalation positive air pressure (IPAP) from a set of five DIP switches 56, and delivers its analog output to terminal I1 of switch 52. Control terminal C is connected to line 42 and receives the inhalation and exhalation signals from phase detection circuit 24. During exhalation, the +10 VDC signal received at terminal C activates switch 52 to provide the EPAP voltage at terminal I2 as the output Vs. During inhalation, the logic low signal at terminal C causes switch 52 to provide the IPAP voltage at terminal I1 as the output Vs.

Error signal Ve is provided to interface 58 which is a conventional interface circuit designed to transform error signal Ve into a signal Vc compatible with valve 14 according to the specifications supplied by the manufacturer. Signal Vc is delivered to power amplifier 66 and is inverted as a corresponding input to power amplifier 68. The net result is a differential voltage output from amplifiers 66 and 68 which is delivered to the terminals of the valve motor of control valve 14, as explained further hereinbelow.

FIGS. 5-8 illustrate preferred control valve 14, which includes valve base 70, shiftable valve element 72 and valve element cover 74. Valve base 70 includes housing 76 and valve motor 78 having motor shaft 80 with locking hole 81 defined in the end thereof.

Housing 76 is preferably composed of synthetic resin material having a generally cylindrical configuration and presents upper and lower sections 82 and 84. Upper section 82 includes upper face 86 having centrally defined opening 88 for receiving motor shaft 80, Which extends upwardly therethrough. Sidewalls 90 of upper section 82 present a slightly smaller diameter than sidewalls 92 of lower section 84 and thereby define shelf 94 for supporting valve cover 74. Housing 76 also includes three, outwardly and upwardly opening recesses 96a, 96b and 96c presenting a generally trapezoidal configuration in cross section. Each recess is defined by lower wall 98, and side walls 100, 102 and 104. Additionally, upper section sidewalls 90 include three outwardly locking bosses 106 located midway between adjacent recesses 96a-c.

Integral valve element 72 includes frusto-conically shaped hub 108, support ring 110, three, pie-shaped, equally spaced, support bodies 114a, 114b and 114c interconnecting hub 108 and support ring 110, and three, rectangularly shaped valve fingers 116a, 116b and 116c equally spaced about the periphery of hub 108 and extending upwardly therefrom. Hub 108 includes hole 118 defined in the lower surface thereof for receiving motor shaft 80. Additionally, hub 108 includes aperture 120 centrally defined through the upper surface thereof for receiving a locking screw therethrough which is further received in motor shaft locking hole 81 for securing element 72 to shaft 80. Hub 108, ring 110 and support bodies 114a-c define three, equally spaced, exhaust ports 122a, 122b and 122c presenting a shape congruent with recesses 96a-c and configured for registration therewith.

Valve element cover 74 includes inverted cup shaped member 124, presenting sidewall 126 and top wall 128, and further includes inlet tube 130, outlet tube 132 and valve fingers 134a, 134b and 134c. Inlet tube 130 is coaxial with cup shaped member 124 at top wall 128 while outlet tube 132 extends outwardly from sidewall 126. Equally spaced fingers 134a-c depend downwardly from inner surface 136 of top wall 128 and are configured intercalate with fingers 116a-c and with the spaces therebetween. Tubular member further includes spaced slots 138 defined in the lower edge of sidewall 126 and configured to register with a corresponding locking boss 106 in order to secure cover 74 to valve base 70.

FIGS. 7 and 8 illustrate assembled control valve 14 with valve fingers 134a-c of cover 74 fitting concentrically about valve fingers 116a-c of rotatable element 72. In operation, pressure controller 26 energizes valve motor 78 in order to rotate element 72 clock-wise or counter clock-wise between a fully closed position (FIG. 7), a fully opened position (FIG. 8), and intermediate positions therebetween.

In the fully closed position of FIG. 7, fingers 116a-c and 134a-c are fully meshed in order to block the respective spaces and ports 122 are in complete registration with recesses 96a-c. In this position, all of the air entering inlet tube 130 from source 12 exhausts through ports 122a-c and recesses 96a-c. In the fully open position of FIG. 8, fingers 116a-c and 134a-c are in registration so that the spaces therebetween are open, and support bodies 114a-c are in registration with and thereby block recesses 96a-c. With this orientation, all of the air is exhausted through outlet tube 132 for delivery to the patient.

The intermediate positions between fully opened and fully closed allow respective portions of the inlet air to exhaust through recesses 96a-c and through outlet tube 132. In this way, control valve 14 provides more precise control over the pressure delivered to the patient, and provides smoother transition between pressure settings.

In the operation of apparatus 10 during inhalation, it is necessary to provide sufficient pressure to maintain the airway pressure splint in the patient in order to prevent occlusion. For patient comfort, however, it is desirable to lower the pressure to a level as low as possible, including ambient pressure, while still maintaining sufficient pressure to keep the airway open. In order to accomplish these benefits, phase detection circuit 24 detects the inhalation and exhalation phases of the patient's respiration, and provides corresponding outputs to pressure controller 14. In the preferred embodiment, controller 14 controls its output pressure in a predetermined manner correlated with inhalation and exhalation as indicated by the outputs received from circuit 24. More particularly, pressure controller 14 controls the pressure delivered to the patient at a higher level during inhalation and a lower level during exhalation as determined by the settings on DACs 48,50. Typically, the respective inhalation and exhalation pressure levels are prescribed by the patient's physician.

FIGS. 9–11 illustrate control valve 140 which is another embodiment of a control valve for use in place of valve 14. Valve 140 includes valve body 142 and actuator assembly 144. Valve body 142 includes external tubular inlet coupler 146 in communication with inlet passage 148, and further includes exhaust passage 150 and outlet passage 152 having external outlet coupler 154 extending therefrom. As illustrated in FIGS. 10–11, exhaust and outlet passages 150,152 communicate with inlet passage 148 and extend transversely therefrom, parallel to one another.

Actuator assembly 144 includes valve motor 156, valve stem 158, exhaust valve element 160 and outlet valve element 162. As illustrated in FIGS. 9–11, motor 156 is coupled to the bottom of body 142 with motor-actuated stem 158 extending upwardly therefrom through, and transverse to, exhaust and outlet passages 150,152. Valve elements 160,162 present oval-shaped configurations and are coupled with stem 158 for rotation therewith. Element 160 is positioned in exhaust passage 150, and element 152 is positioned in outlet passage 152. Valve elements 160,162 function in a manner analogous to conventional butterfly valves. As illustrated, valve elements 160,162 are angularly displaced from one another on stem 158 by about 45°. Valve motor 156 is coupled electrically with pressure controller 26 and receives signals therefrom in the same manner as valve motor 78 or valve 14.

FIGS. 10 and 11 illustrate control valve 140 in the closed/exhaust position. In this position, exhaust valve element 160 is positioned parallel to the air flow and outlet valve element 162 is positioned so that its edges engage the sidewalls of outlet passage 152 to block all outflow. In other words, all of the inlet air entering through inlet passage 148 would exhaust through exhaust passage 150 and none would be provided through outlet passage 152 to the patient. In the open/outlet position, elements 160 and 162 would be rotated clockwise as viewed from above until the edges of exhaust element 160 engage the walls defining exhaust passage 150. In this position, outlet element 162 is positioned parallel to the air flow through outlet passage 152. In this way, no air is exhausted but rather, the full supply is provided through outlet passage 152.

Motor 156 responds to the signals received from pressure controller 26 in order to position valve 140 in the closed or open positions or any intermediate position therebetween. As with control valve 14, this arrangement allows smooth controllable transition between the various valve positions.

Having thus described the preferred embodiment of the present invention the following is claimed as new and desired to be secured by Letters Patent:

1. An apparatus for detecting the inhalation and exhalation phases of a respiratory cycle having associated respiratory gas flow, said apparatus comprising:
    signal production means for producing first and second signals representative of the respiratory gas flow with said signal production means further including means for delaying one of said signals in time relative to the other of said signals; and said signals having respective amplitudes so that one of said signals presents the greater amplitude during at least a portion of one of the phases and so that the other of said signals presents the greater amplitude during at least a portion of the other of said phases; and
    processing means for processing said signals for determining therefrom the occurrence of said respective phases and for producing outputs representative of said phases.

2. The apparatus as set forth in claim 1, said signal production means including flow sensor means for producing said first signal representative of instantaneous respiratory gas flow and time delay means for producing said second signal delayed in time relative to said first signal.

3. The apparatus as set forth in claim 2, further including amplitude scaling means for producing said second signal scaled in amplitude relative to said first signal.

4. The apparatus as set forth in claim 3, said scaling means including means for scaling said amplitude at a first level during one of said phases and means for scaling said amplitude at a second level during the other of said phases.

5. The apparatus as set forth in claim 4, wherein said means for scaling said amplitudes at a first level and a second level are accessible by a patient.

6. The apparatus as set forth in claim 1, said processing means including means for comparing the amplitudes of said first and second signals, for producing a first output when said first signal presents a greater amplitude than said second signal, and for producing a second output when said second signal presents a greater amplitude than said first signal.

7. The apparatus as set forth in claim 1, said first and second signals being electrical signals.

8. The apparatus as set forth in claim 1, said outputs including electrical signals.

9. An apparatus for facilitating the respiration of a patient having respiratory cycle with associated respiratory gas flow and exhibiting inhalation and exhalation phases, said apparatus comprising:
    supply means for supplying a respiratory gas under pressure from a source thereof to a patient;
    means for producing first and second signals representative of the respiratory gas flow with said signal production means further including means for delaying one of said signals in time relative to the other of said signals; and said signals having respective amplitudes so that one of said signals presents the greater amplitude during at least a portion of one of the phases and so that the other of said signals presents the greater amplitude during at least a portion of the other of said phases;
    processing means for processing said signals for determining therefrom the occurrence of said respective phases and for producing outputs representative of said phases; and
    control means coupled with said supply means and said processing means for receiving said outputs and responsive thereto for controlling said respiratory gas pressure to the patient in a predetermined manner correlated with said phases.

10. The apparatus as set forth in claim 9, said control means including means for controlling said respiratory gas pressure at a first pressure level during the inhalation phase and for controlling said respiratory gas pressure at a second pressure level lower than said first level during the exhalation phase.

11. The apparatus as set forth in claim 10, said second pressure level including ambient pressure.

12. The apparatus as set forth in claim 10, said second pressure level including a pressure level greater than ambient.

13. The apparatus as set forth in claim 9, said signal production means including flow sensor means for producing said first signal representative of instantaneous respiratory gas flow and time delay means for producing said second signal delayed in time relative to said first signal.

14. The apparatus as set forth in claim 13, further including amplitude scaling means for producing said second signal scaled in amplitude relative to said first signal.

15. The apparatus as set forth in claim 14, said scaling means including means for scaling said amplitude at a first level during one of said phases and means for scaling said amplitude at a second level during the other of said phases.

16. The apparatus as set forth in claim 15, wherein said means for scaling said amplitudes at a first level and a second level are adjustable by a patient.

17. The apparatus as set forth in claim 9, said processing means including means for comparing the amplitudes of said first and second signals, for producing a first output when said first signal presents a greater amplitude than said second signal, and for producing a second output when said second signal presents a greater amplitude than said first signal.

18. The apparatus as set forth in claim 9, said first and second signals being electrical signals.

19. The apparatus as set forth in claim 9, said outputs including electrical signals.

20. A method for detecting the inhalation and exhalation phases of a respiratory cycle having associated respiratory gas flow, said method comprising:
   producing first and second signals representative of the respiratory gas flow from a signal production means, delaying one of said signal in time relative to the other of said signals, said signals having respective amplitudes, said first signal presents the greater amplitude during at least a portion of the inhalation phase, said second signal presents the greater amplitude during at least a portion of the exhalation phase; and
   processing said signals for determining therefrom the occurrence of said inhalation and exhalation phases and for producing a first output corresponding to the inhalation phase and a second output corresponding to the exhalation phase.

21. The method as set forth in claim 20, wherein said step of producing said first and second signals includes:
   using a flow sensor for producing said first signal, said first signal being representative of instantaneous respiratory gas flow; and
   using time delay means for producing said second signal delayed in time relative to said first signal.

22. The method as set forth in claim 21, further comprising scaling said second signal in amplitude relative to said first signal.

23. The method as set forth in claim 22, wherein said step of scaling said second signal includes:
   using scaling means for scaling the amplitude of an inhalation phase of said second signal to a first level; and
   using said scaling means for scaling the amplitude of an exhalation phase of said second signal to a second level.

24. The method as set forth in claim 23, wherein said step of scaling said second signal includes making said scaling means accessible to a patient.

25. The method as set forth in claim 20, wherein said step of processing said signals further includes:
   comparing the amplitude of said first signal and second signal;
   producing said first output when the amplitude of said first signal is greater than the amplitude of said second signal; and
   producing said second output when the amplitude of said second signal is greater than the amplitude of said first signal.

26. The method as set forth in claim 20, wherein said step of producing said first and second signals includes:
   producing said first signal as an electrical signal; and
   producing said second signal as an electrical signal.

27. The method as set forth in claim 20, wherein said step of processing said signals includes:
   producing said first output as an electrical signal; and
   producing said second output as an electrical signal.

* * * * *